United States Patent [19]

Robertson

[11] Patent Number: 5,374,536

[45] Date of Patent: * Dec. 20, 1994

[54] SYNERGISTIC PRODUCT SELECTION TEST FOR BIOCIDES

[75] Inventor: Linda R. Robertson, St. Charles, Ill.

[73] Assignee: Nalco Chemical Company, Naperville, Ill.

[ * ] Notice: The portion of the term of this patent subsequent to Apr. 27, 2010 has been disclaimed.

[21] Appl. No.: 979,750

[22] Filed: Nov. 23, 1992

Related U.S. Application Data

[63] Continuation-in-part of Ser. No. 670,858, Mar. 18, 1991, abandoned.

[51] Int. Cl.$^5$ .................. C12Q 1/32; C12N 5/00
[52] U.S. Cl. .................. 435/26; 435/4; 435/29; 435/32; 435/34; 435/240.3
[58] Field of Search .............. 435/26, 4, 29, 32, 34, 435/240.3

[56] References Cited

U.S. PATENT DOCUMENTS

| | | | |
|---|---|---|---|
| 3,963,580 | 6/1976 | Vedamuthu | 435/39 |
| 4,479,961 | 10/1984 | Martin | 424/270 |
| 4,595,691 | 6/1986 | LaMarre et al. | 514/367 |
| 4,616,037 | 10/1986 | LaMarre et al. | 514/515 |
| 4,661,503 | 4/1987 | Martier et al. | 514/643 |
| 4,661,517 | 4/1987 | LaMarre et al. | 514/515 |
| 4,661,518 | 4/1987 | LaMarre et al. | 514/528 |
| 4,800,235 | 1/1989 | LaMarre et al. | 514/643 |
| 5,206,151 | 4/1993 | Robertson | 435/32 |

OTHER PUBLICATIONS

Kull et al, *Applied Microbiology*, vol. 9, pp. 538–541, 1961.

Clark, *Water Treatment Institute to Newsletter*, vol. 1, No. 42, pp. 1–5, 1984.

Staneck et al, *J. Clinical Microbiology*, vol. 26, No. 1, pp. 1–7, 1988.

Washington II, et al, *Manual of Clinical Microbiology*, 2nd edition, published by American Society for Microbiol., Chapter 45, pp. 410–417, 1974.

A. J. Zwart Voorspuij and C. A. G. Nass 1957 No. 1–2 Arch Int. Phamacodyn. "Some Aspects of the Notions Additivity, Synergism and Antagonism in the simultaneous Activity of Two Antibacterial Agents in Vitro".

*Primary Examiner*—Michael G. Wityshyn
*Assistant Examiner*—Abdel A. Mohamed
*Attorney, Agent, or Firm*—Robert A. Miller; James J. Drake; Joseph B. Barrett

[57] ABSTRACT

The product selection test is developed for rapid determination of the presence of synergistic blends of the biocide or the presence of biocide blends in contaminated waters. The method uses a reduction oxidation dye system, supplied nutrients, admixtures of one or more biocides or blends thereof and incubation times and temperatures providing for a variation of color changes of the dye system. Industrial waters such as pulp and paper waters contaminated with microbes can be tested by this rapid method of determining the presence of synergistic blends of anti-microbial agents.

9 Claims, 4 Drawing Sheets

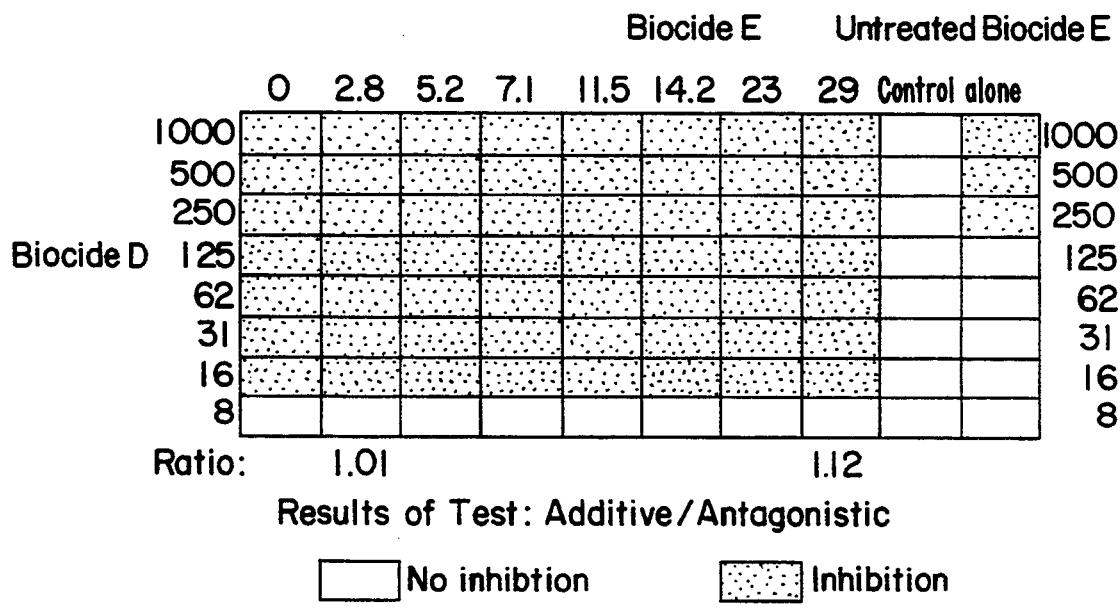
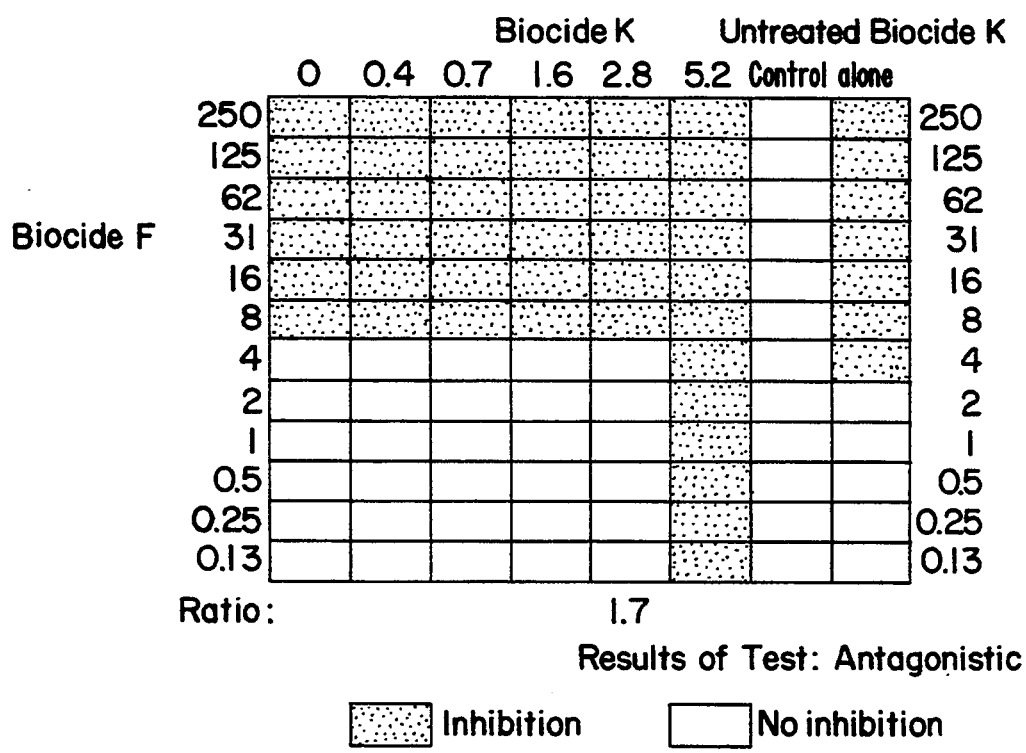

SYNERGISTIC PRODUCT SELECTION TEST FOR BIOCIDES

BACKGROUND OF THE INVENTION

This case is a continuation-in-part of U.S. Ser. No. 07/670,858, filed Mar. 18, 1991, now abandoned.

FIELD OF THE INVENTION

The invention relates to a method for determining minimum inhibitory concentrations of anti-microbial agents and, more particularly, to a method of determining the effects of such anti-microbial agents on one another.

DESCRIPTION OF THE PRIOR ART

Biocides and microbiocides are used to control or eliminate bacterial growth in a number of different industrial aqueous media. Often, one biocide or microbiocide is insufficient to control all bacterial growth in the aqueous medium being treated. The presence of bacterial or other microbiological organisms interferes with the processing of industrial waters being treated and may lead to corrosion and other problems with equipment that is in contact with these contaminated waters.

Recently, as described in U.S. Ser. No. 07/536,390, now U.S. Pat. No. 5,206,151, the disclosure of which is the disclosure of which is incorporated herein by reference, a method has been developed to rapidly determine the effectiveness of biocides and microbiocides in various industrial waters by using a rapid screening technique which takes multiple samples of a contaminated aqueous medium containing microbiological organisms; adds thereto an indicator dye, preferably an oxidation-reduction indicator dye capable of reacting with dehydrogenase enzymes produced by the microbiological organisms; and then adds a nutrient accelerator to the treated solutions containing this oxidation-reduction indicator dye. The treated samples are contained on a titration plate with a serially diluted amount of an anti-microbial agent, and the titration plate is incubated at temperatures equivalent to the operational temperatures of the industrial aqueous systems in which the microbiological organisms exist. This method causes growth and accelerates microbiological organism activity which produces an increased concentration of reducing enzymes which react with the oxidation-reduction indicator dye to cause a change in color. The change in color is then noted.

By comparing the first change in colors in the dyes relative to untreated columns, it is possible to determine the minimum inhibitor concentration (M.I.C.) of anti-microbial agents which inhibit the growth of the microbiological organisms contained in the contaminated aqueous system.

Although the test above provides a great improvement in the art in terms of the ability to rapidly measure the effectiveness of anti-microbial agents in contaminated industrial aqueous systems, it is limited in its teaching to the use of a single biocide or a single mixture of biocides in industrial aqueous systems.

The presence of synergism, antagonism, or mere additive results is determined according to the industrially accepted method described by S. C. Kull, P. C. Elsman, H. D. Sylwestrowicz, and R. L. Mayer in *Applied Microbiology*, Volume 9, pages 538-541, (1961) the disclosure of which is included herein by reference. In addition, the teachings of Kull, et al are presented in U.S. Pat. No. 4,661,518, issued to LaMarre, et al, the disclosure of which is also incorporated herein by reference.

In addition to the articles cited above, the following U.S. patents have been noted where synergistic combinations of various biocides have been determined using old techniques, which techniques often require several days to obtain the results. These patents include:

U.S. Pat. No. 4,661,503, Martin, et. al.
U.S. Pat. No. 4,661,517, Martin, et. al.
U.S. Pat. No. 4,661,518, Martin, et. al.
U.S. Pat. No. 4,800,235, LaMarre et. al.

the disclosures of which are incorporated herein by reference.

SUMMARY OF THE INVENTION

Desirably, a method would exist that would provide a way to determine the existence of synergistic, additive, or antagonistic effects in mixtures of at least two anti-microbial agents in microbiologically contaminated waters. It is an object of Applicant's invention to provide for a rapid method of determining the existence of synergistic, additive or antagonistic mixtures of biocides that can provide the results of such a determination within a period ranging from 30 minutes to about six to eight hours.

It is also an object of this invention to particularly determine the existence of synergistic, additive or antagonistic mixtures of biocides in pulp and paper processing waters including, but not limited to paper furnish, various cellulosic dispersions, white waters, paper mill effluent waters, cellulosic fiber suspensions and slurries, recycle streams, and the like. Also, Applicant's method may be used for screening of synergistic blends of experimental or known biocides which may be useful in synthetic paper mill furnishes, which synthetic furnishes are inoculated with known strains of bacteria.

The rapid test for determining the existence of synergistic, additive, or antagonistic mixtures of microbiocides in microbiologically contaminated waters is a method comprising the steps of:

(a) Obtaining a known volume of microbiologically contaminated waters from an industrial aqueous system and admixing therewith a known amount of a nutrient mixture, thereby forming a nutriated contaminated water sample.

(b) Adding known aliquots of the nutriated contaminated water sample to separate sample wells on a titration plate, which titration plate contains at least three columns of sample wells, whereby each column contains at least three rows of said sample wells.

(c) Adding a sample of a first biocide to each row and subsequently serially diluting down the column, row by row, to obtain a first biocide-treated titration plate having, in each column, a serially diluted first biocide containing admixtures of nutriated contaminated waters.

(d) Separately mixing in containers, vessels, beakers, and the like, which are not the titration plate sample wells, another known aliquot of the contaminated waters with a second biocide to obtain a second biocide-treated contaminated water sample.

(e) Adding the second biocide-treated water sample, at a chosen concentration, to each well of a first colum, and then serially diluting in each column of the titration plate. A separate column is treated with the same serial dilution of the second biocide, but is maintained free of the first biocide to prepare a blank of the second biocide. Simultaneously, a separate and different column is created on the plate which contains serially diluted concentrations of the first biocide, as a blank for the first biocide.

After adding, in each column of the titration plate of step (c) above, row by row, a serially diluted and known amount of the stock solution of the second biocide so as to obtain in each column a known, and identical, concentration of the second microbiocide, Applicant has effectively formed on the same dual titration plate, a dual treated titration plate containing separate rows containing constant concentrations of the first biocide and variable concentrations of the second biocide and also containing separate columns of constant concentrations of the second biocide and variable concentrations of the first biocide, as well as these so called "blank" columns, one containing only contaminated waters and nutrients, a second additionally containing only the first biocide, and a third additionally containing only the second biocide.

(f) Adding a known concentration of a redox dye to each well of each column and row of the dual treated titration plate which dye is capable of reacting, and changing color by said reaction, with reducing enzymes created by the accelerated growth processes occurring in the nutriated contaminated water samples in each well. Each well is adequately mixed to insure homogenous solutions.

The titration plate then contains columns and rows as described above, each row containing constant concentrations of the first microbiocide and variable concentrations of the second microbiocides and each column containing variable concentrations of the first microbiocide and constant concentrations of the second microbiocide. Each sample well on the dual treated titration plate also contains redox dyes, preferably resazurin, nutrient, and the contaminated waters being tested.

The titration plate is then incubated at relatively constant temperatures, which temperatures preferably range from about 10° C. to about 90° C., and most preferably range between temperatures which are within ±15° C. of the temperature, preferably ±10° C. of the temperature, of the contaminated waters being treated, as these waters occur in their normal environment.

Usually, incubation occurs under normal atmospheric, or aerobic, conditions. Optionally, the atmosphere may be changed to create an anaerobic atmosphere such as an atmosphere under carbon dioxide, nitrogen, argon, helium or mixtures thereof, and the like. An enriched oxygen atmosphere could also be used.

The completed dual treated titration plate is incubated for a time period sufficient to allow for the growth of nutriated microbes and reaction of the microbes in the reducing enzymes. This provides a color change in each column and each row where biocidal activity can control microbiological growth, that is, where the concentration of antimicrobial agent is high enough. The incubation time can range from as little as 30 minutes and often is completed within a period of 6-8 hours.

After incubation, a colorimetric analysis is conducted for each well in each column and row and compared with the blanks containing untreated samples, and with the blank columns having sample wells containing only treatments with the first biocide and sample wells containing treatments only with the second biocide.

By making the colorimetric analysis, it is possible to use standard methods for determining synergistic, additive, or antagonistic results from the mixtures of biocides being tested.

When the terms, first biocide and second biocide, are used herein, it is meant to include the use of not only a single biocide, but also simple mixtures of two or more biocides, in a single first mix, as the first and/or second biocide.

BRIEF DESCRIPTION OF DRAWINGS

FIG. 2 shows a combination inhibition titration grid (titration plate) on actual so called, "Clear Well" liquor obtained in a pulp and paper mill using Biocides F and D, as well as, Biocides E and D.

FIG. 4 shows an antogonistic result obtained when Biocides F and K were tested on a blend chest furnish from a commercial paper mill.

DETAILED DESCRIPTION OF THE PREFERRED EMBODIMENT ANTI-MICROBIAL AGENTS

Figure 1A:
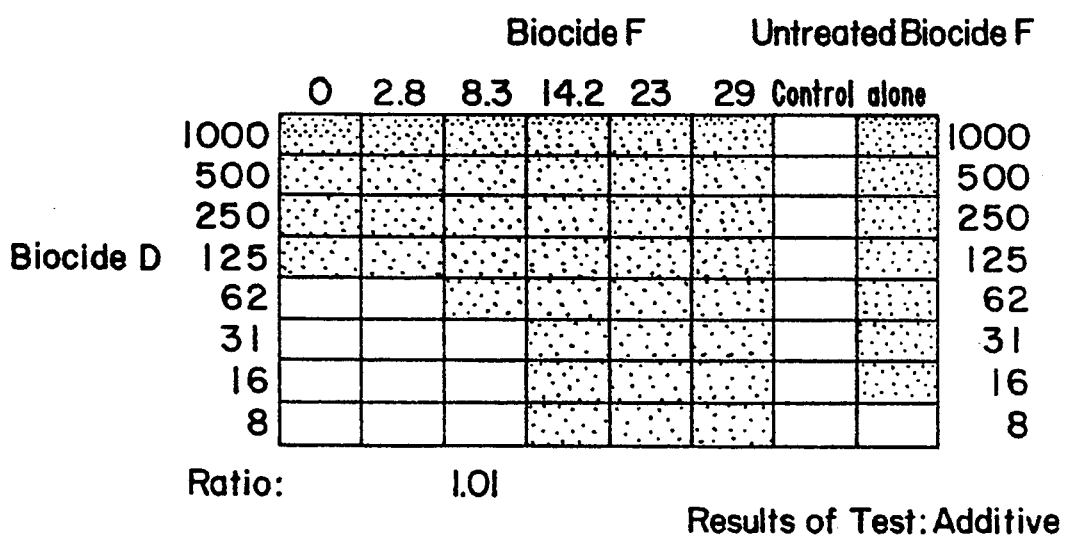
FIGS. 1A and 1B provide a synergistic study for two different combinations of biocides using *Pseudomonas aeruginosa* in a synthetic furnish. Biocide F and Biocide D (see Table I) and Biocide F and a Biocide K are tested with the results of the tests being graphically displayed in FIGS. 1A and 1B, respectively. A representation of the incubated dual treated titration plate is presented.
Figure 1B:
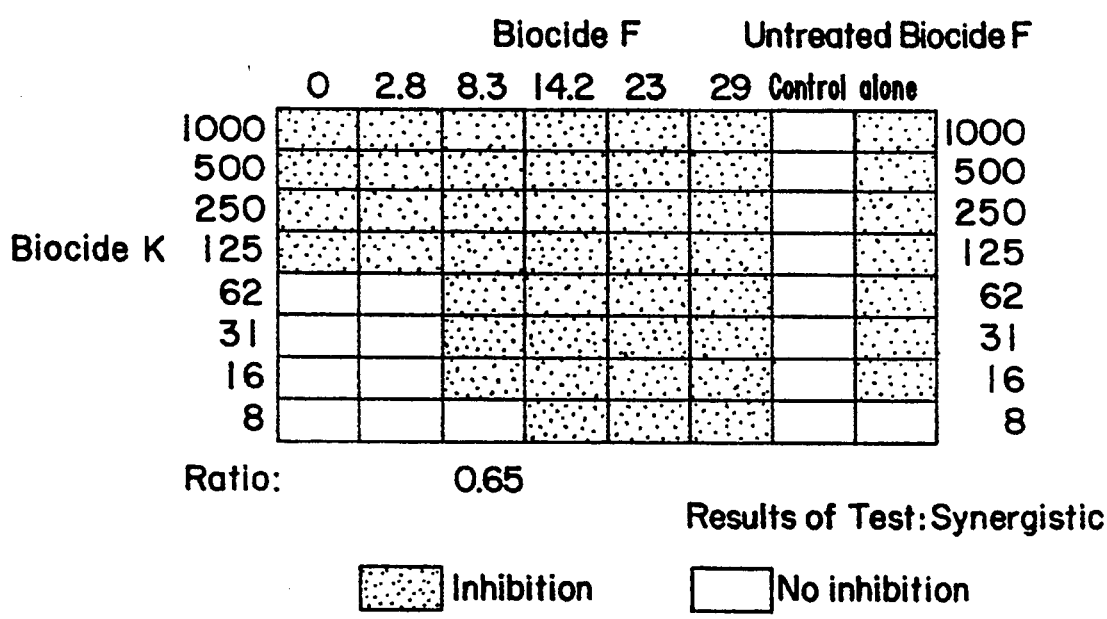
Figure 3A:
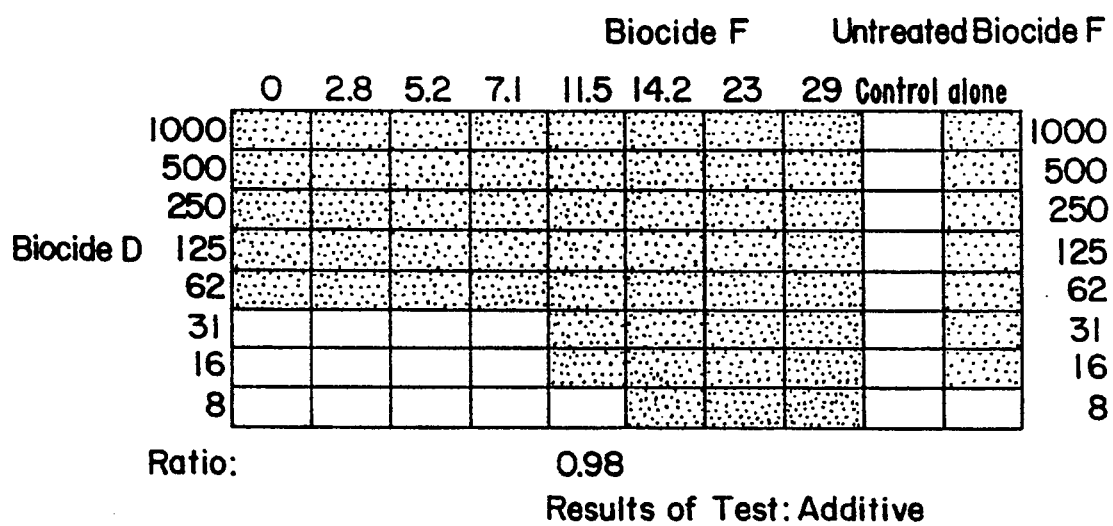
FIGS. 3A and 3B show actual tests on so called "Save-All" Liquors from a pulp and paper mill using Biocides F and D and Biocides E and D with the results of both tests being displayed in FIGS. 3A and 3B, respectively.
Figure 3B:
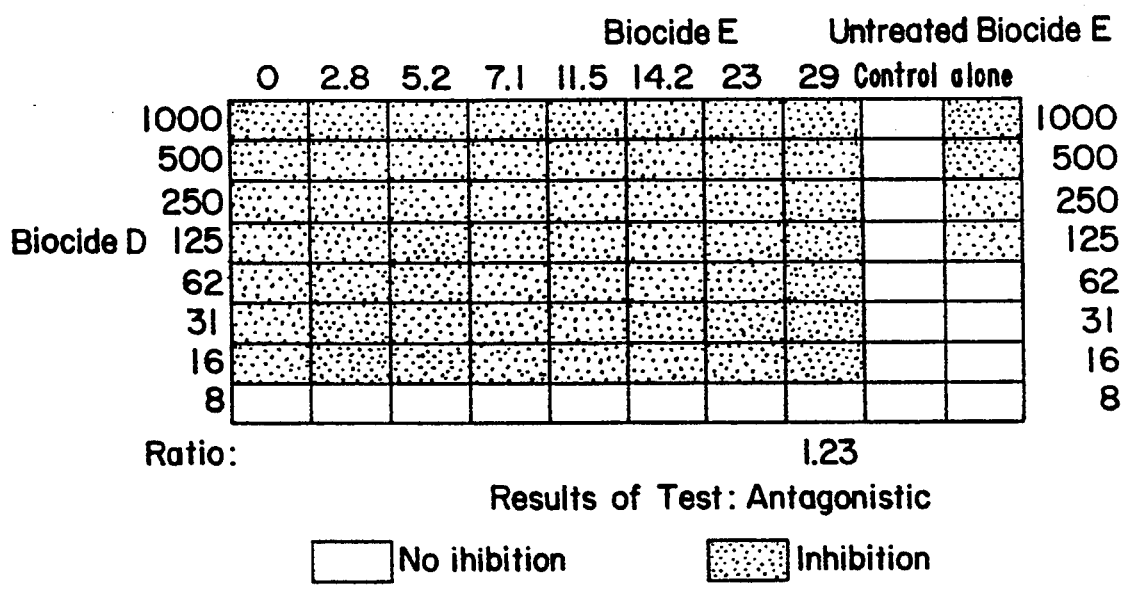
Figure 5:
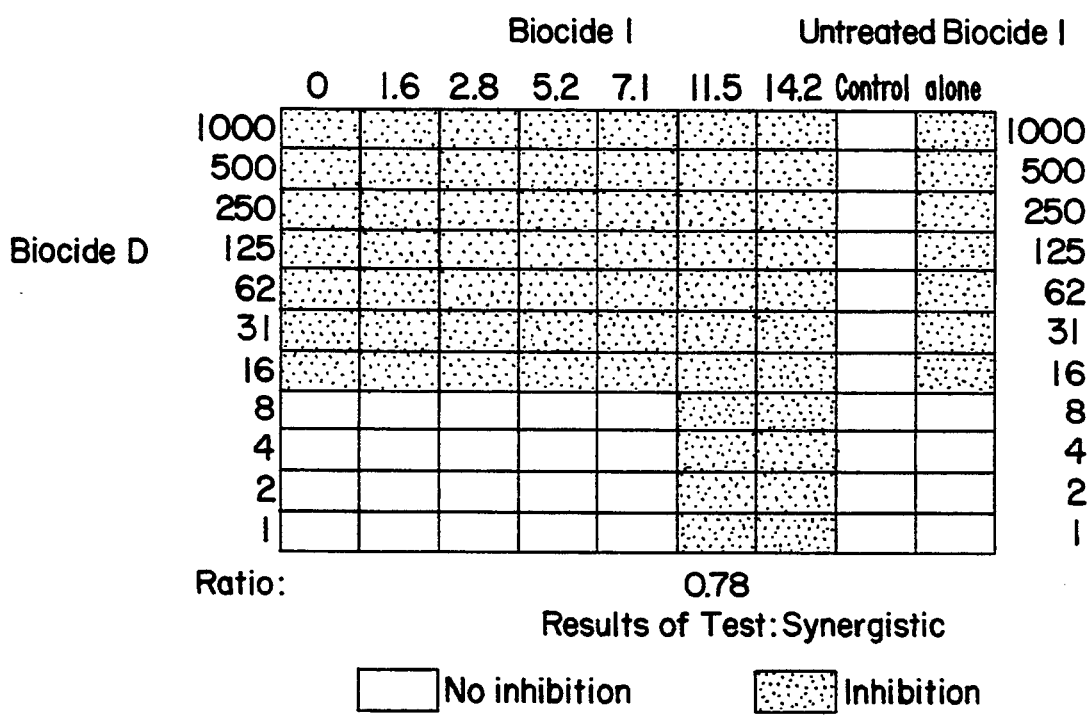
FIG. 5 shows tests using Biocides I and D on a mixed pulp furnish obtained from a second pulp and paper mill.
Figure 6:
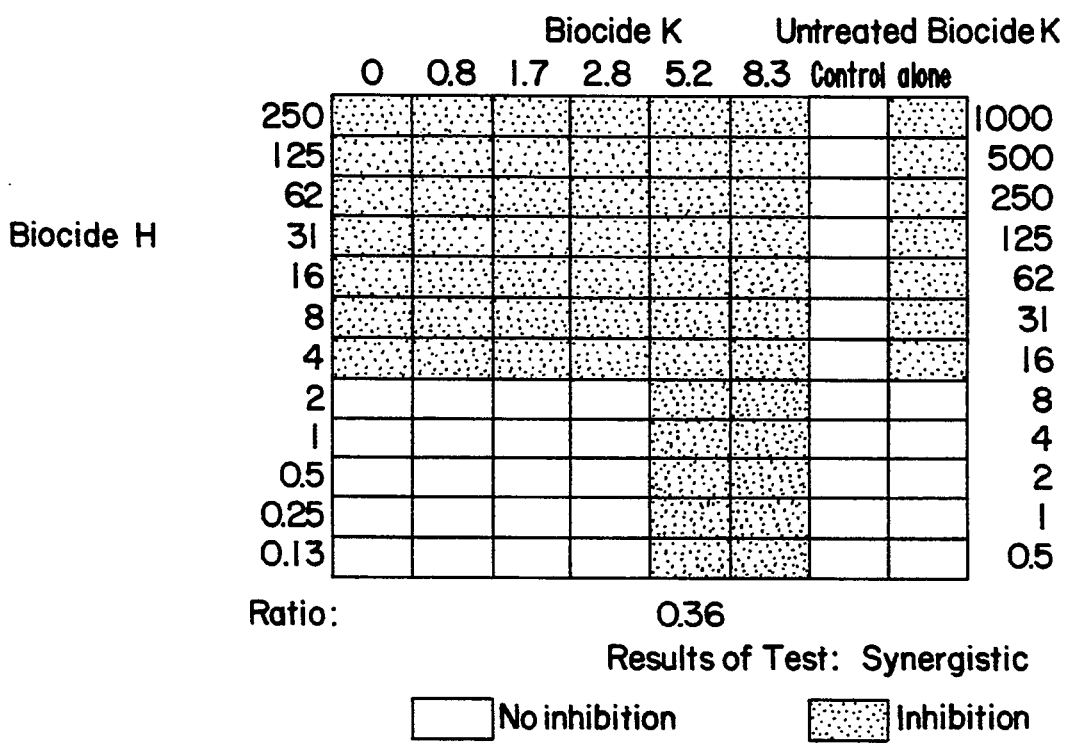
FIG. 6 again uses a mixed furnished from a paper mill and test Biocides H and K and indicates synergistic results.

By the term anti-microbial agent, microbiocide or biocide, we mean to include any agent or chemical or admixture thereof containing at least one, or a blend of one or more biocides. As examples of these biocides, which examples are not intended to be limiting, a list of biocides and blends thereof are described in Table 1. In Table 1, various biocides which will be exemplified later are identified in terms of their chemical actives and in terms of a typical use. However, these materials may be used in a number of ways other than the use specified.

TABLE 1

| Biocide | BIOCIDE Actives | Typical Use |
| --- | --- | --- |
| A | 3,5-Dimethyl-tetrahydro-2H-1,3,5-thiadiazine-2-thione | Preservative for starch and clay |
| B | Methylene bisthiocyanate | Slimicide |
| C | 1-Alkyl(C16–18)amino-3-aminopropane acetate & Bis(trichloromethyl) sulfone | Slimicide |
| D | 5-Chloro-2-methyl-4-isothiazolin-3-one & 2-Methyl-4-isothiazolin-3-one | Slimicide Preservative |
| E | Alkyl dimethylbenzyl-ammonium chloride & Dialkyl methyl benzylammonium chloride | Slimicide |

TABLE 1-continued

BIOCIDE

| Biocide | Actives | Typical Use |
|---|---|---|
| F | 2,2-Dibromo-3-nitrilo-propionamide (DBNPA) | Slimicide |
| G | 2-(Thiocyanomethylthio)-benzothiazole & Bis(trichloromethyl) sulfone | Slimicide |
| H | Sodium dimethyldithiocarbamate & Disodium ethylene bis-dithiocarbamate | Slimicide |
| I | Glutaraldehyde (1,5 pentanediol) | Slimicide |
| J | 1-(3-Chloroallyl)-3,5,7-triazo-niaadamatane chloride | Preservative |
| K | N-4-Dihydroxy-alpha oxobenzene chloride | Slimicide |
| L | Sodium hypochlorite | |
| M | 4,5-dichloro-1,2-dithio-3-one | |
| N | Decylthioethylamine | |

CONTAMINATED INDUSTRIAL AQUEOUS WATERS

The contaminated aqueous waters or water systems are preferably chosen from the groups consisting of paper stock or paper furnish or other cellulosic fiber dispersions or other aqueous solutions or dispersions obtained in pulp and paper manufacture, including but not limited to, white waters, brown stock waters, fiber furnish dispersions, pulp and paper plant effluent waters, and the like. In addition, our contaminated waters may include open recirculation cooling waters, waste effluent streams, chemical process waters, food processing waters, textile processing waters, refinery waters, refinery effluent waters, fermentation streams, and the like.

THE REDUCTION—OXIDATION INDICATOR DYES

As to the choice of reduction oxidation indicator dyes, the indicator dye preferably is chosen from the resazurin/redox couple which consists of resazurin, resorufin, and hydroresorufin. These chemical structures are provided below:

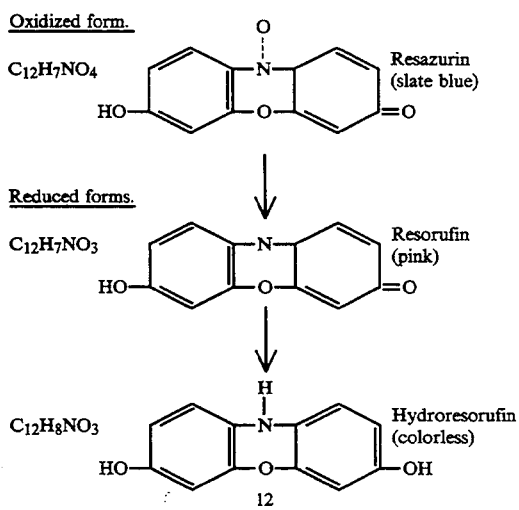

In our process, the use of resazurin is preferred since the reduction of resazurin to resorufin provides a useful color change, from pink to blue. However, in very high population of microorganisms, and in the absence of sufficient inhibiting amounts of anti-microbial agent, the reducing chemicals produced by nutriated microorganisms can drive this reduction all the way to hydroresorufin, which is colorless. In addition to the above resazurin based reduction-oxidation indicator dye system, other reduction oxidation indicator dye compounds can include the following:

Tetrazolium Violet
2-(p-Iodophenyl)-3-(p-nitrophenyl)-5-phenyl-tetrazolium chloride
Methylene Blue
Formazan Dyes The preferred reduction oxidation indicator dye is resazurin and the resazurin reaction products described above. Formazan dyes which form highly colored compounds which are also easily visualized or spectrophotometrically determined in our techniques. When using the resazurin dyes, particularly coupled with the resorufin reduced form of the indicator dye system, the color of the oxidized form of this dye is blue and the color of the reduced form is pink. As earlier stated, if highly intense reducing compounds are present, or if they are present in much higher concentrations, this pink color can be changed to a clear, colorless solution indicating the presence of hydroresorufin.

NUTRIENTS

The nutrients useful in our invention, which nutrients are added in aliquot amounts to the known volumes of contaminated waters, include any nutrient which is capable of being in solution or suspension with water or any mixture of such nutrients. These nutrients can include glucose, sucrose, fructose, glycerol, beef extract, peptone, nutrient broth (which is a combination of beef extract and peptone), tryptone, milk, pasteurized half and half creamer, yeast extract, or any mixture of the above. Specific nutrients to be preferred in the use of our rapid method of determining the presence of synergism of two or more microbiocides normally includes a mixture of glucose, nutrient broth, and pasteurized half and halfcreamer, in an approximate weight ratio of approximately 10:5:4. However, these nutrients may be blended in any reasonable ratios, one to the other, for example, from 1:3-8:10 to 10:3-8:1, and used successfully to accelerate microbiological organism activity. This accelerates metabolism rates and the formation of the reducing compounds, specifically the dehydrogenase enzymes, which reducing compounds react with the reduction oxidation indicator dyes useful in the invention. The nutrients are added to the microbiologically contaminated solutions either before addition to the microtitation plate or directly on the microtitration plate. Microbiological activity and microbial respiration is thereby increased and metabolism rates or metabolic processes of these microorganisms are increased providing the results described above. The interaction of these reducing chemicals and enzymes with the redox indicator dyes provides a way of monitoring cell viability via the various organisms' cellular electron transfer systems and also provides, by these interactions, the ability to measure the synergistic antagonistic, or mere additive effects of the various microbiocides.

MICROTITRATION PLATES

The microtitration plates used are preferably clear plastic plates which contain multiple columns of depressions, or sample wells. Preferably, the microtitration plate contains at least three columns, most preferably at least four columns and primarily contains from 8 to 12 columns. Each column contains at least three rows of sample wells, preferably at least four rows of sample wells and most preferably can contain from 6 to 12 rows of sample wells.

Most preferably the microtitration plate contains from about 8 to about 12 rows of sample wells in from about 8 to 12 columns. The plates, however, may also be manufactured from white ceramic materials or other plate-like construction providing for a proper background to allow easy visual reading or spectrophotometric visualization of the color changes observed. The titration plates most useful may be obtained from Costar Corporation, Cambridge, Mass.

PROCEDURES

As earlier stated, our method of determining the existence of synergistic, additive, or antagonistic mixtures of microbiocides in microbiologically contaminated waters comprises the collection of known volumes or aliquots of the contaminated waters, the admixture of these known volumes with a known and reproducible amount in each sample well in each titration plate of nutrient, and the addition of the contaminated water plus nutrient mixture in known volumes to each sample well contained in each column and row of a titration plate. Separately, the contaminated waters are collected in known volume and are combined with a known concentration of a first microbiocide, or microbiocide mixture, thereby obtaining a first biocide-contaminated water standard solution. Using multiple pipettes, a known concentration, typically from about 10 to about 1,000 parts per million, of the first biocide is added to the top row of the columns on the microtitration plate, which sample wells contain the nutriated contaminated waters of the first admixture described above. The first column comprises high concentrations of first biocide-contaminated water sample wells which are then serially diluted down the columns of the titration plate to obtain a titration plate containing identical concentrations of contaminated waters, identical concentrations of nutrient and serially diluted concentrations of the first biocide.

This is accomplished by adding the first biocide-contaminated water materials singly to a first horizontal row of wells and then serially diluting by using prior furnished nutrient admixtures in the well to create a plate having at least six columns of at least six rows of variable concentrations of nutrient-contaminated water-first biocide containing sample wells. The serial dilution techniques are then repeated for each row of sample wells contained in each column on the titration plate, down each row. Each row therefore contains a constant but serially diluted first biocide, row by row, and each column has variable, and serially diluted, concentrations of the first biocide.

A separate mixture is made of a second biocide and the contaminated waters. The second mixture is of a known concentration of second biocide in a known volume of contaminated waters. These concentrations may also range from about 0.025 to 1000 ppm of the second biocide, or biocide mixture.

Using the second biocide/contaminated water aliquot mixture, a blank column is prepared by serially diluting each well of the column containing contaminated waters with the sample of the secondary biocide water mixture, and adding nutrients so as to provide a column containing only the secondary biocide in nutriated, contaminated waters. Also, the dual treated titration plate needs to contain an untreated control column where each well contains the nutrient mixture, the redox dye, and the contaminated waters, but no biocide.

Then, a known volume of stock solution of the secondary biocide is added to each column in a known but serially dilute and different concentration of the second biocide thereby forming separate rows containing a constant concentration of the first biocide, and a variable and serially diluted concentration of the second biocide. Simultaneously the titration plate also contains separate columns containing variable concentrations of the first biocide and constant concentrations of the second biocide.

Then, known concentrations of redox dyes are added to each sample well on the titration plate. A column is maintained on the titration plate which is treated only with the first biocide in serially diluted manner, and likewise a column is created, as taught above, having been treated with only the second biocide. The dual treated titration plate then contains multiply diluted columns and multiply diluted rows of first and second biocides and blank columns containing only first biocide treated and second biocides treated nutriated contaminated waters.

After redox dyes are added, the plates are incubated at temperatures ranging from 10° C. to about 90° C., preferably between about 20° C. and 80° C., and most preferably within ±15° of the temperature in the environment from which the contaminated waters were obtained. This incubation may be done under normal atmospheric conditions, that is an aerobic incubation, or it may done anaerobically by providing, over the titration plate, an atmosphere of carbon dioxide, nitrogen, argon, helium or mixtures thereof. Incubation is done in an enclosed cabinet, preferably containing the desired atmosphere and controlled at the desired temperature, and designed preferably to contain at least one, but preferably more than one dual treated titration plate.

The incubation period ranges from about 30 minutes to about from 4 to 8 hours, at which time color development is determined and compared against the color development in each serially diluted column containing only the first biocide and/or only the second biocide.

The results are then compared using the techniques taught in U.S. Pat. No. 4,616,037 as provide by the Kull, et al, teaching earlier described.

By using these techniques, it is easily determined when the presence of certain of these mixtures of biocides provide for a synergistic result, when the mixture of these biocides provide for a mere additive result, and when the mixture of these biocides provide for an antagonistic result.

The incubation time and test period time and readout time is considerably shorter and considerably more sensitive to the presence of both minimum inhibitory concentrations of each of the anti-microbial agents than earlier known techniques. The results provide a determination of synergism, addition, or antagonism within a period of time considerably shorter than that period of time currently used with normal techniques. In addition, the technique is easily applied in the field where the samples can be immediately taken and tested. Additionally the results are available and these techniques can be applied even in non-sterile conditions.

After the initial dual treatment titration plate has been developed at chosen concentrations of each of the individual biocides, and some indication of synergism has been obtained, the test can be repeated with titration plates which are readjusted in terms of concentrations of one or both of the biocides to refine the determination of the synergistic result.

It is preferred that the pH's of aqueous test systems, particularly those solutions using the resazurin dyes, are adjusted between a pH ranging from about 4 to about 9, preferably between about 5 to 8. Most preferably, the pH's should be adjusted to a pH ranging from 6 to 8. However, it is most preferable that the test be performed at the Ph of the aqueous system as found in the environment which the microorganisms provide for contamination. If the contaminated water pH's are below 6, other dyes such as the tetrazolium violet or the Iodophenyl-nitrophenyl-phenyltetrazolium chloride dyes as earlier mentioned may be used. These dyes are less sensitive to low Ph.

The disclosed method of determining synergism, antagonism, or additive results when testing two or more biocides is particularly useful when the contaminated waters are paper stock or paper furnish waters obtained from various locations in a pulp and paper manufacturing mill. Preferably, in such a contaminated water system, the redox indicator dyes are chosen from the group consisting of tetrazolium violet, 2-(p-Iodophenyl)-3-(p-nitrophenyl)-5-phenyl-tetrazolium chloride, and resazurin. In pulp and paper systems, the nutrients are preferably chosen from nutrient broth, glucose, milk, diary half and half ultra pasteurized creamer, and mixtures thereof.

The titration plates contain at least 3, preferably 4, and most preferably at least 6–8 columns, each column containing at least 3, preferably at least 6 and most preferably at least 8 sample wells. As before, the microtitration plates are made of glass, ceramic, clear plastics, or any other media which may tolerate the incubation temperatures, chemical exposures, and time periods, and which provide a reasonable background from which the color changes may be observed and interpreted. The treated titration plates are most preferably incubated at temperatures ranging from 30° C. to about 60° C. for a period of time ranging from about 30 minutes to about 6–8 hours. Incubation as before may be done under aerobic or anaerobic conditions. To provide further information about our method for determining the presence of synergistic additive or antagonistic results, the following examples are given.

EXAMPLES

A series of figures are presented which figures indicate the results obtained on fully incubated titration plates treated according to the techniques described above with various anti-microbial agents. Each of these diagrams demonstrate a color change when antimicrobial concentrations are not sufficient to control microbiological growth, which color change is compared in blank columns versus the multiply treated columns and rows at various concentrations of first and second biocides. If control of growth occurs, no color change occurs. Each of these results were obtained by incubation of appropriate contaminated waters, which contaminated waters had been nutriated, treated with the redox dye, treated with one or both biocides in decreasing serially diluted concentrations, and incubated at times ranging from about 4 to about 6 hours. Nutrient concentrations were at effective concentrations to increase microbial growth so that results can be obtained within at least 10 hours, or less.

The figures indicate either additive, synergistic, or antagonistic results depending upon the biocide combination used.

The results of the synergistic, additive, or antagonistic results are available from the formula:

$$\frac{Qa}{QA} + \frac{Qb}{QB} = X$$

wherein Qa is the quantity of first biocide producing, in admixture, an end-point QA is the quantity of first biocide producing alone an end-point Qb is the quantity of second biocide producing, in admixture, an end-point QB is the quantity of second biocide producing alone an end-point.

The value of X is then determined.

If X is less than one, a synergy combination is present;

If X is equal to one, an additive combination is present; and

If X is greater than one, an antagonistic combination is present.

Having described my invention, I claim:

1. A method of determining the existence of synergistic, additive, or antagonistic mixtures of microbiocides in microbiologically contaminated paper furnish waters which method comprises the steps of:
   (a) adding a known quantity of an aliquot mixture containing a determined volume of microbe contaminated waters, an oxidation-reduction indicator dye which reacts with dehydrogenase enzymes, and nutrients which accelerate microbial organism activity to a series of columns and rows of sample wells on a titration plate containing at least five columns of at least three rows of said sample wells, wherein the nutrients are selected from the group consisting of half and half dairy creamer, yeast extract, glucose, sucrose, fructose, glycerol, peptone, half extract, tryptone, milk and mixtures thereof, and then
   (b) adding to all but two columns of said sample wells a serially diluted amount of a single first microbiocide, maintaining two untreated columns on said titration plate; and then
   (c) adding to each row of all but one column containing the first microbiocide, a serially diluted amount of a second microbiocide, retaining two untreated columns, and then
   (d) treating one of the untreated columns with a serially diluted amount of the second microbiocide, maintaining the second column of the untreated columns free of either the first or the second microbiocide, thereby forming a treated titration plate, and then
   (e) incubating said treated titration plate at temperatures essentially equivalent to system temperatures of the contaminated waters for a period of time sufficient to develop a change in the color of the indicator dye, which color change is caused by the reaction of the indicator dye with reducing chemicals and enzymes produced by nutrient acceleration of microbiological metabolism, and then
   (f) comparing the change in color of the mutually biocidally treated columns with the change of color in the columns treated only with a single microbiocide, and then (g) determining by said comparing the existence of synergistic, additive, or antagonistic mixtures of the two microbiocide in the contaminated waters being treated.

2. The method of claim 1 wherein the first and second microbiocides are different and are chosen from the group consisting of: 3,5-Dimethyl-tetrahydro- 2H-1,3,5-thiadiazine-2-thione, Methylene bisthiocyanate, Dodecylquandine hydrochloride, 1-Alkyl(C16–18)amino-3-aminopropane acetate & Bis(trichloromethyl) sulfone, 5-Chloro-2-methyl-4-isothiazolin-3-one & 2-Methyl-4-isothiazolin-3-one, Alkyl dimethylbanzl-ammonium chloride & Dialkyl methyl banzyl- ammonium chloride, 2,2-Dibromo-3-nitrilo-propionamide (DBNPA), 2-(Thiocyanomethylthio)-benzothiazole & Bis(thichloromethyl) sulfone, Sodium dimethyldithiocarbamate & Disodium ethylene bis-dithiocarbamate, Glutaraldehyde (1,5 pentanediol), 1-(3-Chloroallyl)-3,5,7-triazo-niaadamatane chloride, N-4-Dihydroxy-alpha-oxobenzene ethanimidoyl chloride, Sodium hypochlorite, 4,5-dichloro-1,2-dithiol 3-one, Decylthioethylamine, and mixtures thereof.

3. The method of claim 1 wherein the microbiologically contaminated paper furnish waters are selected from the group consisting of pulp and paper processing waters, paper mill furnish waters, paper mill white waters, brown stock waters, paper mill effluent waters, open recirculating cooling waters, closed recirculating cooling waters, boiler feed waters, sugar mill processing waters, food processing waters, and petroleum and refinery processing and effluent waters.

4. The method of claim 1 wherein the microbiologically contaminated paper furnish waters comprise furnish waters inoculated with known bacterial cultures.

5. The method of claim 1 wherein the treated titration plate is incubated under atmospheres chosen from the group consisting of an aerobic atmospheres, an anaerobic atmosphere and a carbon dioxide atmosphere.

6. The method of claim 1 wherein the indicator dye is selected from the group consisting of resazurin, tetrazolium violet and 2-(p-iodophenyl)-3-(p-nitrophenyl)-5-phenyl-tetrazolium chloride.

7. A method of determining synergistic, additive, or antagonistic mixtures of microbial agents for a microbe contaminated water which comprises:

(a) obtaining a known volume of said water;

(b) adding thereto a known volume of nutrient mixture, thereby forming a nutriated contaminated water;

(c) adding a known aliquot of the nutriated contaminated water to each sample well of each column and row of a titration plate, thereby forming a non-treated titration plate; and then (d) using a multiple pipette, adding a known amount of a first biocide to the top row of all but two columns, wherein a concentration of biocide in said top row ranges from about 10 ppm to about 1000 ppm, based on total treated, nutriated contaminated water; and then (e) serially diluting each row of each first microbiocide-treated column to obtain a first biocide-treated titration plate having a constant concentration of first biocide in each row, and columns of serially diluted first biocide; and then (f) forming a standard solution of a second biocide in said contaminated water, wherein the concentration of said second biocide ranges from about 0.5 to about 1000 ppm, based on total solution; and then (g) adding to a first column of the first biocide-treated titration plate a constant concentration of the second biocide and serially diluting same across the rows of sample wells, thereby obtaining a dual treated titration plate having constant concentration of second biocide in each column, serially diluted concentration of second biocide in each row, constant concentration of first biocide in each row, and serially diluted first biocide in each column, and then, providing for at least one column of each serially diluted first and second biocide alone; and then (h) adding to each sample well a redox dye which reacts with reducing chemicals and enzymes to provide a color change, and then incubating said dual treated titration plate at temperatures ranging from 10° to 90° C. for a time sufficient to provide a color change; and then (i) comparing the color changes in the dual treated rows and columns with the color change of the columns treated alone with the first and second biocides and determining the existence of synergism, addition, or antagonism.

8. The method of claim 7 in which the contaminated waters is selected from the group consisting of pulp and paper processing waters, pulp and paper effluent waters, pulp and paper recycle waters, white waters, brown stock waters, and mixtures thereof, and further, wherein the first and second biocides are both, separately and independently, selected from the group consisting of: 3,5-Dimethyl-tetrahydro- 2H-1,3,5-thiadiazine-2-thione, Methylene bisthiocyanate, Dodecylquandine hydrochloride, 1-Alkyl(C16–18)amino-3-aminopropane acetate & Bis(trichloromethyl) sulfone, 5-Cholor-2-methyl-4-isothiazolin-3-one & 2-Methyl-4-isothiazolin-3-one, Alkyl dimethylbenzyl-ammonium chloride & Dialkyl methyl benzyl-ammonium chloride, 2-,2-Dibromo-3-nitrilopropionamide (DBNPA), 2-(Thiocyanomethylthio)-benzothiazole & Bis(trichloromethyl) sulfone, Sodium dimethyldithiocarbamate & Disodium ethylene bis-dithiocarbamate, Glutaraldehyde (1,5 pentanediol), 1-(3-Chloroallyl)-3,5,7-triazoniaadamatane chloride, N-4-Dihydroxy-alpha-oxobenzene ethanimidoyl chloride, Sodium hypochlorite, 4,5-dichloro-1,2-dithiol 3-one, Decylthioethylamine, and mixtures thereof.

9. The method of claim 8 wherein the contaminated water comprises waters inoculated with known bacterial cultures.

* * * * *